(12) United States Patent
Daifuku et al.

(10) Patent No.: US 10,479,807 B2
(45) Date of Patent: Nov. 19, 2019

(54) SILYLATED PYRIMIDINE PRODRUGS AND METHODS OF THEIR USE

(71) Applicant: EPIGENETICS PHARMA LLC, Mercer Island, WA (US)

(72) Inventors: Richard Daifuku, Mercer Island, WA (US); Dmitri S. Sergueev, Bothell, WA (US)

(73) Assignee: Epigenetics Phrama LLC, Mercer Island, WA (US)

(*) Notice: Subject to any disclaimer, the term of this patent is extended or adjusted under 35 U.S.C. 154(b) by 0 days.

(21) Appl. No.: 15/516,653

(22) PCT Filed: Oct. 8, 2015

(86) PCT No.: PCT/US2015/054755
§ 371 (c)(1),
(2) Date: Apr. 3, 2017

(87) PCT Pub. No.: WO2016/057828
PCT Pub. Date: Apr. 14, 2016

(65) Prior Publication Data
US 2017/0305941 A1 Oct. 26, 2017

Related U.S. Application Data

(60) Provisional application No. 62/061,526, filed on Oct. 8, 2014.

(51) Int. Cl.
*A61K 31/695* (2006.01)
*C07F 7/18* (2006.01)
*C07H 19/12* (2006.01)
*C07H 19/06* (2006.01)
*A61P 35/02* (2006.01)

(52) U.S. Cl.
CPC .......... *C07F 7/1804* (2013.01); *A61K 31/695* (2013.01); *A61P 35/02* (2018.01); *C07F 7/1872* (2013.01); *C07H 19/06* (2013.01); *C07H 19/12* (2013.01)

(58) Field of Classification Search
CPC .................................................. C07F 7/1872
See application file for complete search history.

(56) References Cited

U.S. PATENT DOCUMENTS

| | | | |
|---|---|---|---|
| 5,120,842 A | 6/1992 | Failli et al. | |
| 6,413,945 B1 | 7/2002 | Tremont et al. | |
| 8,703,932 B2 | 4/2014 | Cherukupally et al. | |
| 8,716,445 B2 | 5/2014 | Lal et al. | |
| 9,073,960 B2 | 7/2015 | Beigelman et al. | |
| 2006/0205685 A1 | 9/2006 | Phiasivongsa et al. | |
| 2008/0261918 A1 | 10/2008 | Showell et al. | |

FOREIGN PATENT DOCUMENTS

| | | |
|---|---|---|
| EP | 0378706 B1 | 12/1994 |
| WO | 2004050665 A1 | 6/2004 |
| WO | 2004050666 A1 | 6/2004 |
| WO | WO 2006/070985 A1 | 7/2006 |

OTHER PUBLICATIONS

Siedlecki et al. (Biochemical and Biophysical Research Communications, 2003, 306, 558-563).*
Chou, T. S., et al., "Stereospecific Synthesis of 2-Deoxy-2,2-difluororibonolactone and Its Use in the Preparation of 2'-Deoxy-2',2'-difluoro-β-D-ribofuranosyl Pyrimidine Nucleosides: The key role of selective crystallization," Synthesis, 565-570 (1992).
Christman, J.K., "5-Azacytidine and 5-aza-2'-deoxycytidine as inhibitors of DNA methylation: mechanistic studies and their implications for cancer therapy," Oncogene, vol. 21; 5483-5495 (2002).
Gemzar for injection, Eli Lilly and Company, Indianapolis, IN; 20 pages (2007).
Hong, D. S., et al., "Phase 1 Study to Determine the Safety and Pharmacokinetics of Oral Administration of TAS-102 in Patients With Solid Tumors", Cancer vol. 107; No. 6; 1383-1390 (2006).
Iyer, A. K., et al., "Exploiting the enhanced permeability and retention effect for tumor targeting," Drug Discovery Today, vol. 11; No. 17-18; 812-818 (2006).
Mini, E., et al., "Cellular pharmacology of gemcitabine," Annals of Oncology, vol. 17(Suppl 5); v7-v12 (2006).
Plunkett, W., et al., "Gemcitabine: metabolism, mechanisms of action and self-potentiation," Semin. Oncol.; vol. 22(4; Suppl 11); 3-10 (1995) (abstract only).
PubChem, CID 15780809, Feb. 12, 2007, pp. 1-9 [online] [retrieved on Apr. 12, 2017] from the internet URL: https://pubchem.ncbi.nlm.nih.gov/compound/15780809.
PubChem, CID 524952, Mar. 27, 2005, pp. 1-11 [online] [retrieved on Apr. 12, 2017] from the internet URL: https://pubchem.ncbi.nlm.nih.gov/compound/524952.
Vadlamudi, S., et al., "Effect of combination Treatment with 5-Azacytidine and Cytidine on the Life-Span and Spleen and Bone Marrow Cells of Leukemic (L1210) and Nonleukemic Mice," Cancer Res.; vol. 30; 362-369 (1970).
Assadi, M.G., et al. (2006) "Synthesis and characterization of methylsalicylate and acetaminophen silyl ether canditates for prodrugs" Main Group Chemistry, 5:3, 179-190 (abstract only).
Beisler, J. et al. "Synthesis and antitumor activity of dihydro-5-azacytidine", Journal of Medicinal Chemistry, 20(6): 806-812 (1977).
Extended European Search Report for EP Application No. 15848354.5 "Vitamin E-Nucleoside Prodrugs", dated Apr. 30, 2018.
Mahkam, M., et al., "pH-sensitive hydrogel containing acetaminophen silyl ethers for colon-specific drug delivery", Designed Monomers and Polymers, 9(6): 607-615 (2006).
Piskala, et al. "Preparation of Some Derivatives of 5-Azacytidine and 2.-Deoxy-5-azacytidine", Collection Symposium Series (XIIITH Symposium on Chemistry of Nucleic Acid Components, Czech Republic; Sep. 3-9, 2; [Collection Symposium Series], XX, vol. 61, 1996, pp. S23-S25.

(Continued)

Primary Examiner — Brian E McDowell
(74) Attorney, Agent, or Firm — Hamilton, Brook, Smith & Reynolds, P.C.

(57) ABSTRACT

Silylated-pyrimidine prodrugs, compositions that include the silylated-pyrimidine prodrugs, methods for making the silylated-pyrimidine prodrugs and compositions, and methods for treating cancer using the silylated-pyrimidine prodrugs and compositions.

11 Claims, 1 Drawing Sheet

(56) References Cited

OTHER PUBLICATIONS

Antiretroviral Agents: Nucleoside Analogues, LiverTox, NIH, accessed Aug. 23, 2018 at https://livertox.nih.gov/NucleosideAnalogues.htm.
Galmarini, C.M., et al., "Nucleoside analogues: mechanisms of drug resistance and reversal strategies", Leukemia (2001) 15, 875-890.
Daifuku, R., et al., "NUC041, a Prodrug of the DNA Methytransferase Inhibitor 5-aza-2',2'-Difluorodeoxycytidine (NUC013), Leads to Tumor Regression in a Model of Non-Small Cell Lung Cancer", Pharmaceuticals 2018, 11, 36, 15 pages.

\* cited by examiner

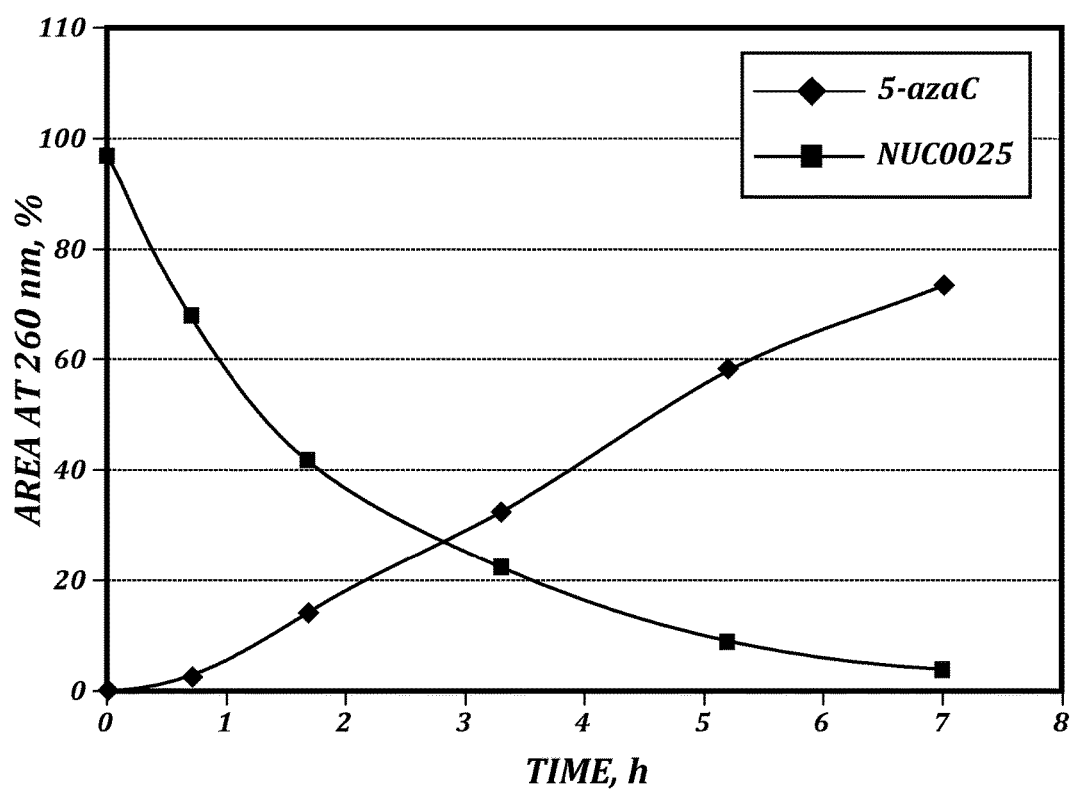

SILYLATED PYRIMIDINE PRODRUGS AND METHODS OF THEIR USE

CROSS-REFERENCE TO RELATED APPLICATION

This application is the U.S. National Stage of International Application No. PCT/US2015/054755, filed Oct. 8, 2015, which designates the U.S., published in English, and claims the benefit of U.S. Patent Application No. 62/061,526, filed Oct. 8, 2014. The entire teachings of the above applications are incorporated herein by reference.

FIELD OF THE INVENTION

The present invention provides silylated-pyrimidine prodrugs, compositions that include the silylated-pyrimidine prodrugs, methods for making the silylated-pyrimidine prodrugs and compositions, and methods for treating cancer using the silylated-pyrimidine prodrugs and compositions.

BACKGROUND OF THE INVENTION

Pyrimidine analogs are known to be effective chemotherapeutic agents. Gemcitabine, an analog of cytidine with a modified sugar, a 2',2'-difluorodeoxyribose, is a chemotherapeutic drug currently approved as single therapy for the treatment of pancreatic cancer, and as part of combination chemotherapy regimens for the treatment of non-small cell lung cancer, breast cancer and ovarian cancer (Gemzar (gemcitabine HCl) for injection. 2007. Eli Lilly and Company.) The following properties make gemcitabine an effective anticancer agent: (1) it is an inhibitor of ribonucleoside diphosphate reductase (RR), the enzyme that catalyses the conversion of diphosphorylated ribonucleosides to diphosphorylated deoxyribonucleosides; (2) it acts as a DNA chain terminator; and (3) it is not a substrate for pyrimidine nucleoside phosphorylase, hence precluding the breakdown of a nucleoside into a separate base and a sugar moiety (Plunkett, W., et al., "Gemcitabine: Metabolism, Mechanism of Action and Self-Potentiation," *Semin. Oncol.* 22(4; Suppl 11):3-10, 1995; Mini, E., et al., "Cellular Pharmacology of Gemcitabine," *Ann. Oncol.* 17 (Suppl 5) v7-v12. 2006).

Two other cytidine analogs, 5-azacytidine and 5-azadeoxycytidine, are approved for the treatment of hematologic tumors, and act by inhibiting DNA methyl transferase (DNMT), the enzyme required for DNA methylation. The 5-azacytidine analogs are known to be unstable in water and cleaved at the 6-position of the base (Christman, J. K., "5-azacytidine and 5-aza-2'-deoxycytidine as Inhibitors of DNA Methylation: Mechanistic Studies and Their Implications for Cancer Therapy, *Oncogene* 21:5483-5495, 2002.)

Trifluridine, 5-trifluorothymidine, has also demonstrated antineoplastic activity and is thought to act by inhibiting thymidilate synthase. However, its development as an antineoplastic agent has been hampered by its short half-life (12 minutes). Co-administration of trifluridine with a thymidine phosphorylase inhibitor has resulted in more acceptable pharmacokinetics with mean half-lives between 1.37 and 1.57 hours (Hong D S, Abbruzzese J L, Bogaard K et al. Phase I study to determine the safety and pharmacokinetics of oral administration of TAS-102 in patients with solid tumors. Cancer. 2006; 15(107):1383-1390.)

One approach that has been proposed to prolong the circulatory half-life of pyrimidine analogs is to generate a prodrug that would result in a more hydrophobic molecule that could be formulated in a lipid based nanoformulation and rapidly release the active drug upon exposure to an aqueous environment at the tumor site. Conjugating a drug that has a short half-life with a lipophilic moiety such as, for example, trimethylsilyl (TMS) or other silyl moieties, and formulating the lipophilic prodrug in a hydrophobic milieu may result in a prolonged circulating half-life.

There continues to exist a need for novel cancer therapeutics with improved efficacy, safety, and/or pharmacokinetic profiles. The invention provides novel silylated-pyrimidine prodrugs and compositions for the treatment of cancer.

SUMMARY OF THE INVENTION

The present invention provides therapeutic drug compounds that are silylated-pyrimidine prodrugs, compositions that include the silylated-pyrimidine prodrugs, methods for making the silylated-pyrimidine prodrugs, and methods for treating cancer using the silylated-pyrimidine prodrugs and compositions.

In one aspect of the invention, silylated-pyrimidine prodrugs are provided. The silylated-pyrimidine prodrugs of the invention are pyrimidine analogs having a silyl group attached at one or more hydroxyl positions of the ribose sugar. In one embodiment, the silylated-pyrimidine prodrugs are analogs of cytidine. In one embodiment, a silylated-pyrimidine prodrug is a trimethylsilyl analog of cytidine. In one embodiment, the silylated-pyrimidine prodrugs are analogs of thymidine. In one embodiment a silylated-pyrimidine prodrug is a trimethylsilyl analog of thymidine. Methods for making the silylated-pyrimidine prodrugs are also provided.

In one embodiment, the invention provides a silylated pyrimidine compound having the formula:

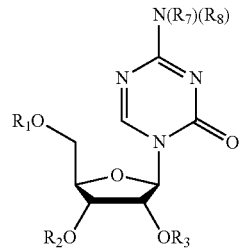

wherein $R_1$, $R_2$, $R_3$, $R_7$, and $R_8$ are independently selected from hydrogen or $Si(R_4)(R_5)(R_6)$, wherein $R_4$, $R_5$, and $R_6$ are independently selected from hydrogen or alkyl, provided that at least one of $R_1$, $R_2$, $R_3$, $R_7$, or $R_8$ is $Si(R_4)(R_5)(R_6)$. In another embodiment, the invention provides a compound having the formula:

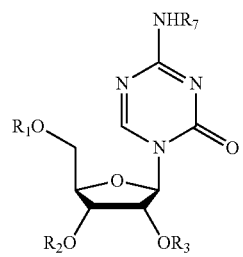

wherein $R_1$, $R_2$, $R_3$, and $R_7$ are independently selected from hydrogen or $Si(R_4)(R_5)(R_6)$, wherein $R_4$, $R_5$, and $R_6$ are independently selected from hydrogen or alkyl, provided that at least one of $R_1$, $R_2$, $R_3$, or $R_7$ is $Si(R_4)(R_5)(R_6)$. In a further embodiment, the invention provides a compound having the formula:

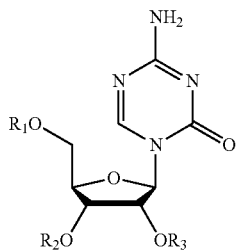

wherein $R_1$, $R_2$, and $R_3$ are independently selected from hydrogen or $Si(R_4)(R_5)(R_6)$, wherein $R_4$, $R_5$, and $R_6$ are independently selected from hydrogen or alkyl, provided that at least one of $R_1$, $R_2$, or $R_3$ is $Si(R_4)(R_5)(R_6)$. In a particular embodiment, the invention provides a compound wherein $R_1$, $R_2$, and $R_3$ are $Si(R_4)(R_5)(R_6)$ and $R_4$, $R_5$, and $R_6$ are methyl.

In a second embodiment, the invention provides a silylated pyrimidine compound having the formula:

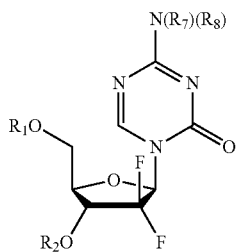

wherein $R_1$, $R_2$, $R_7$, and $R_8$ are independently selected from hydrogen or $Si(R_4)(R_5)(R_6)$, wherein $R_4$, $R_5$, and $R_6$ are independently selected from hydrogen or alkyl, provided that at least one of $R_1$, $R_2$, $R_7$, or $R_8$ is $Si(R_4)(R_5)(R_6)$. In another embodiment, the invention provides a compound having the formula:

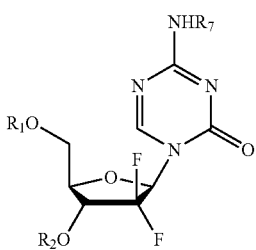

wherein $R_1$, $R_2$, and $R_7$ are independently selected from hydrogen or $Si(R_4)(R_5)(R_6)$, wherein $R_4$, $R_5$, and $R_6$ are independently selected from hydrogen or alkyl, provided that at least one of $R_1$, $R_2$, or $R_7$ is $Si(R_4)(R_5)(R_6)$. In a further embodiment, the invention provides a compound having the formula:

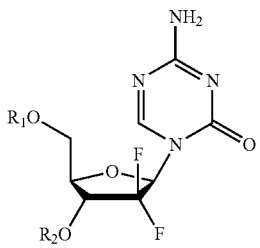

wherein $R_1$ and $R_2$ are independently selected from hydrogen or $Si(R_4)(R_5)(R_6)$, wherein $R_4$, $R_5$, and $R_6$ are independently selected from hydrogen or alkyl, provided that at least one of $R_1$ or $R_2$ is $Si(R_4)(R_5)(R_6)$. In a particular embodiment, the invention provides a wherein $R_1$ and $R_2$ are $Si(R_4)(R_5)(R_6)$ and $R_4$, $R_5$, and $R_6$ are methyl.

In a third embodiment, the invention provides a silylated pyrimidine compound having the formula:

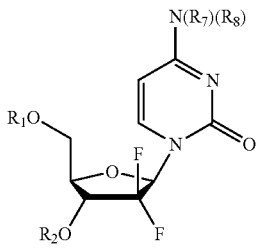

wherein $R_1$, $R_2$, $R_7$, and $R_8$ are independently selected from hydrogen or $Si(R_4)(R_5)(R_6)$, wherein $R_4$, $R_5$, and $R_6$ are independently selected from hydrogen or alkyl, provided that at least one of $R_1$, $R_2$, $R_7$, or $R_8$ is $Si(R_4)(R_5)(R_6)$. In another embodiment, the invention provides a compound having the formula:

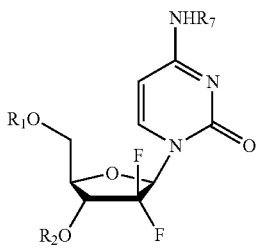

wherein $R_1$, $R_2$, and $R_7$ are independently selected from hydrogen or $Si(R_4)(R_5)(R_6)$, wherein $R_4$, $R_5$, and $R_6$ are independently selected from hydrogen or alkyl, provided that at least one of $R_1$, $R_2$, or $R_7$ is $Si(R_4)(R_5)(R_6)$. In a further embodiment, the invention provides a compound having the formula:

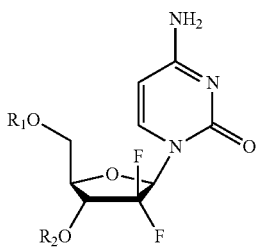

wherein $R_1$ and $R_2$ are independently selected from hydrogen or $Si(R_4)(R_5)(R_6)$, wherein $R_4$, $R_5$, and $R_6$ are independently selected from hydrogen or alkyl, provided that at least one of $R_1$ or $R_2$ is $Si(R_4)(R_5)(R_6)$. In a particular embodiment, the invention provides a compound wherein $R_1$ and $R_2$ are $Si(R_4)(R_5)(R_6)$ and $R_4$, $R_5$, and $R_6$ are methyl.

In a fourth embodiment, the invention provides a silylated pyrimidine compound having the formula:

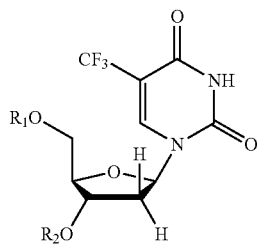

wherein $R_1$ and $R_2$ are independently selected from hydrogen or $Si(R_4)(R_5)(R_6)$, wherein $R_4$, $R_5$, and $R_6$ are independently selected from hydrogen or alkyl, provided that at least one of $R_1$ or $R_2$ is $Si(R_4)(R_5)(R_6)$. In another embodiment, the invention provides a compound wherein $R_1$ and $R_2$ are $Si(R_4)(R_5)(R_6)$ and $R_4$, $R_5$, and $R_6$ are methyl.

In a fifth embodiment, the invention provides a silylated pyrimidine compound having the formula:

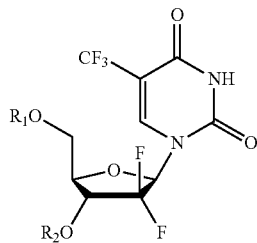

wherein $R_1$ and $R_2$ are independently selected from hydrogen or $Si(R_4)(R_5)(R_6)$, wherein $R_4$, $R_5$, and $R_6$ are independently selected from hydrogen or alkyl, provided that at least one of $R_1$ or $R_2$ is $Si(R_4)(R_5)(R_6)$. In a particular embodiment, the invention provides a compound wherein $R_1$ and $R_2$ are $Si(R_4)(R_5)(R_6)$ and $R_4$, $R_5$, and $R_6$ are methyl.

In another aspect, the invention provides compositions that include the silylated-pyrimidine prodrugs of the invention. The compositions include one or more of the silylated-pyrimidine prodrugs, a pharmaceutically acceptable carrier or diluent, and optionally, one or more additional therapeutic agents. The compositions are useful for the administration of silylated-pyrimidine prodrugs to treat cancer. Methods for making the silylated-pyrimidine prodrug compositions are also provided.

In another aspect of the invention, methods for treating cancer using the silylated-pyrimidine prodrugs and compositions are provided.

In one embodiment, the invention provides a method for delivery of a therapeutic pyrimidine to a tumor site by enhanced permeability and retention, comprising administering an effective amount of a pharmaceutical composition of the invention to subject in need thereof.

In another embodiment, the invention provides a method for treating a cancer, comprising administering an effective amount of a pharmaceutical composition of the invention to subject in need thereof.

In further embodiment, the invention provides a method of treating a solid tumor carcinoma, comprising administering a therapeutically effective amount of a pharmaceutical composition of the invention to a subject in need thereof. Representative solid tumor carcinomas include breast, non-small cell lung, and colon carcinomas.

In yet another embodiment, the invention provides a method of treating a hematological malignancy, comprising administering a therapeutically effective amount of a pharmaceutical composition of the invention to a subject in need thereof. Representative hematologic malignancies include leukemias.

In the methods noted above, in certain embodiments, the subject is a human.

BRIEF DESCRIPTION OF THE DRAWING

FIG. 1 illustrates the release of 5-azacytidine from a representative silyl-pyrimidine compound of the invention (NUC025) in phosphate buffered saline (PBS) at 20° C.

DETAILED DESCRIPTION OF THE INVENTION

The present invention provides therapeutic drug compounds that are silylated-pyrimidine prodrugs, compositions that include the silylated-pyrimidine prodrugs, methods for making the silylated-pyrimidine prodrugs and compositions, and methods for treating cancer using the silylated-pyrimidine prodrugs and compositions.

As noted above, 5-azacytidine and derivatives are unstable in water with hydrolytic cleavage of the cytosine ring. This presents challenges with drug reconstitution, and is one factor adversely affecting circulatory half-life, and perhaps clinical effectiveness. Developing prodrugs of 5-azacytidines is complicated by this instability because certain motifs may increase instability. For example, adding a fatty acid carrier moiety at the N4-amino, such as was done for DHADC (5,6-dihydro-5-azadeoxycytidine) to increase oral bioavailability and prevent deamination, has been assumed to be a risk for increasing the instability of the cytosine. Indeed, it is possible to envision a scenario where a prodrug results in the predominant delivery of the inactive species to the site of the tumor (see, for example, reaction pathways for ring opening and hydrolysis of 5-azacytosine residue in DNA in solution and after covalent linkage to the active site of a DNMT described in Christman J K, Oncogene 21:5483-5495, 2002). One possible remedy is to deliver 5-aza prodrugs that can be formulated in a hydrophobic matrix to the tumor site. Such a properly formulated matrix will not only prevent hydrolysis but may provide other benefits, such as enhanced permeability and retention (EPR).

EPR is the property by which certain sizes of molecules or formulations (such as lipid nanodroplets) tend to accumulate in tumor tissue at a higher concentration than in normal tissues. Tumors are dependent on blood supply from a neovasculature for their nutritional and oxygen supply. These newly formed tumor vessels are usually abnormal in form and architecture. They have poorly-aligned defective endothelial cells with wide fenestrations allowing entry of nanodroplets. Furthermore, tumor tissues usually lack effective lymphatic drainage. Thus nanodroplets can penetrate tumor sites preferentially and are more slowly cleared, leading to accumulation of the active drug at the tumor site.

The size of the nanodroplet is a critical design parameter governing their tumor penetration abilities. Because tumor transport is a diffusion-limited process, nanoparticles of a smaller size (≤20 nm) are found almost universally to diffuse more efficiently through tumor tissue than particles of a larger size (≥100 nm).

Formulating a 5-aza nucleoside in a hydrophobic nanodroplet requires that the 5-aza nucleoside prodrug be hydrophobic and that the carrier moieties be rapidly released at the tumor site, prior to hydrolytic cleavage of the cytosine ring. Such a role can be fulfilled by modifying the OH groups of the sugar or the $NH_2$ group of the base with silyl groups, such as trimethylsilyl (TMS). TMS has been shown to be relatively non-toxic, other than sedation, in studies conducted in a number of animal species for NASA by Corning. Intraperitoneal or intravenous administration of 100-200 mg/kg of TMS resulted in rapid absorption of TMS and blood levels of 1 mg/mL necessary for light anesthesia in rodents. Given the molecular weights of pyrimidines and TMS, it is unlikely that levels producing toxicity would be reached following administration of a therapeutic dose of a medicinal pyrimidine.

Modifying a nucleoside with a silyl group is described herein. In a representative embodiment, 5-azacytidine was modified with TMS to provide 2',3',5'-tri(trimethylsilyl)-5-azacytidine (NUC025) as described in Example 6.

In one aspect of the invention, silylated-pyrimidine prodrugs are provided. In one embodiment, the silylated-pyrimidine prodrugs are analogs of cytidine. In one embodiment, a silylated-pyrimidine prodrug is a trimethylsilyl analog of cytidine. In one embodiment the silylated-pyrimidine prodrugs are analogs of thymidine. In one embodiment a silylated-pyrimidine prodrug is a trimethylsilyl analog of thymidine.

In one embodiment, the present invention provides a silylated prodrug of 2',2'-difluoro-5-azadeoxycytidine having the structure:

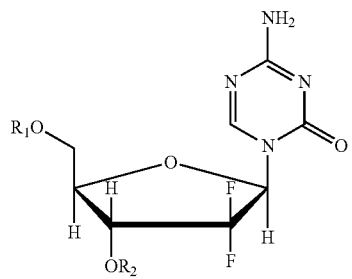

wherein $R_1$ and $R_2$ are independently selected from hydrogen or $Si(R_3)(R_4)(R_5)$, wherein $R_3$, $R_4$, and $R_5$ are independently selected from hydrogen or alkyl, provided that at least one of $R_1$ or $R_2$ is $Si(R_3)(R_4)(R_5)$. In one embodiment, $R_1$ is $Si(R_3)(R_4)(R_5)$ and $R_2$ is hydrogen. In another embodiment, $R_1$ is hydrogen and $R_2$ is $Si(R_3)(R_4)(R_5)$. In a further embodiment, $R_1$ and $R_2$ are $Si(R_3)(R_4)(R_5)$. In one embodiment, $R_3$, $R_4$, and $R_5$ are methyl.

In one embodiment, the present invention provides a silylated prodrug of 2',2'-difluoro-5-azadeoxycytidine, trimethylsilyl-2',2'-difluoro-5-azadeoxycytidine having the structure:

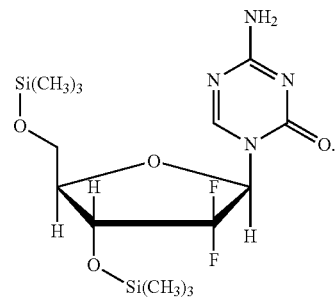

In one embodiment, the present invention provides a silylated prodrug of 2',2'-difluoro-5,6-dihydro-5-azadeoxycytidine having the structure:

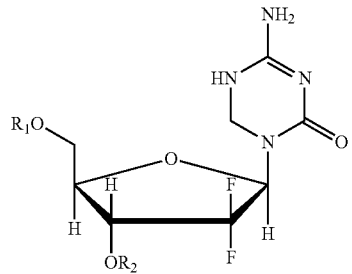

wherein $R_1$ and $R_2$ are independently selected from hydrogen or $Si(R_3)(R_4)(R_5)$, wherein $R_3$, $R_4$, and $R_5$ are independently selected from hydrogen or alkyl, provided that at least one of $R_1$ or $R_2$ is $Si(R_3)(R_4)(R_5)$. In one embodiment, $R_1$ is $Si(R_3)(R_4)(R_5)$ and $R_2$ is hydrogen. In another embodiment, $R_1$ is hydrogen and $R_2$ is $Si(R_3)(R_4)(R_5)$. In a further embodiment, $R_1$ and $R_2$ are $Si(R_3)(R_4)(R_5)$. In one embodiment, $R_3$, $R_4$, and $R_5$ are methyl.

In one embodiment, the present invention provides a silylated prodrug of 2',2'-difluorozebularine having the structure:

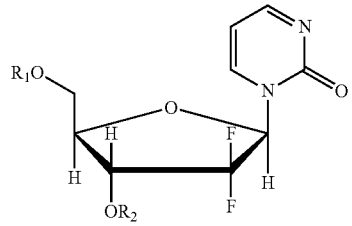

wherein $R_1$ and $R_2$ are independently selected from hydrogen or $Si(R_3)(R_4)(R_5)$, wherein $R_3$, $R_4$, and $R_5$ are independently selected from hydrogen or alkyl, provided that at least one of $R_1$ or $R_2$ is $Si(R_3)(R_4)(R_5)$. In one embodiment, $R_1$ is $Si(R_3)(R_4)(R_5)$ and $R_2$ is hydrogen. In another embodiment, $R_1$ is hydrogen and $R_2$ is $Si(R_3)(R_4)(R_5)$. In a further embodiment, $R_1$ and $R_2$ are $Si(R_3)(R_4)(R_5)$. In one embodiment, $R_3$, $R_4$, and $R_5$ are methyl.

In one embodiment, the present invention provides a silylated prodrug of 2',2'-difluoro-5,6-dihydro-5-azazebularine having the structure:

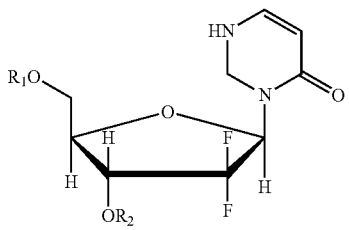

wherein R₁ and R₂ are independently selected from hydrogen or Si(R₃)(R₄)(R₅), wherein R₃, R₄, and R₅ are independently selected from hydrogen or alkyl, provided that at least one of R₁ or R₂ is Si(R₃)(R₄)(R₅). In one embodiment, R₁ is Si(R₃)(R₄)(R₅) and R₂ is hydrogen. In another embodiment, R₁ is hydrogen and R₂ is Si(R₃)(R₄)(R₅). In a further embodiment, R₁ and R₂ are Si(R₃)(R₄)(R₅). In one embodiment, R₃, R₄, and R₅ are methyl.

In one embodiment, the present invention provides a silylated prodrug of 2',2'-difluorodeoxyribose-trifluorothymidine having the structure:

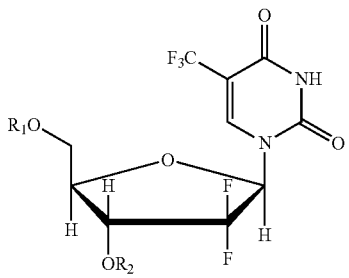

wherein R₁ and R₂ are independently selected from hydrogen or Si(R₃)(R₄)(R₅), wherein R₃, R₄, and R₅ are independently selected from hydrogen or alkyl, provided that at least one of R₁ or R₂ is Si(R₃)(R₄)(R₅). In one embodiment, R₁ is Si(R₃)(R₄)(R₅) and R₂ is hydrogen. In another embodiment, R₁ is hydrogen and R₂ is Si(R₃)(R₄)(R₅). In a further embodiment, R₁ and R₂ are Si(R₃)(R₄)(R₅). In one embodiment, R₃, R₄, and R₅ are methyl.

In one embodiment, the present invention provides a silylated prodrug of azacytidine having the structure:

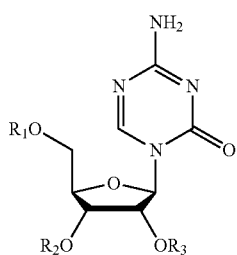

wherein R₁, R₂, and R₃, are independently selected from hydrogen or Si(R₄)(R₅)(R₆), wherein R₄, R₄, and R₆ are independently selected from hydrogen or alkyl, provided that at least one of R₁, R₂, or R₃, is Si(R₄)(R₅)(R₆). In one embodiment, R₁ is Si(R₃)(R₄)(R₅) and R₂ and R₃ are hydrogen. In another embodiment, R₁ is hydrogen, R₂ is Si(R₃)(R₄)(R₅), and R₃ is hydrogen. In a further embodiment, R₁ and R₂ are hydrogen and R₃ is Si(R₃)(R₄)(R₅). Similarly, the invention provides all possible combinations in which two of R₁, R₂, or R₃ are Si(R₃)(R₄)(R₅). In one embodiment, each of R₁, R₂, and R₃ is Si(R₃)(R₄)(R₅). In one embodiment, R₄, R₅, and R₆ are methyl.

In other embodiments, the invention provides the cytidine prodrugs noted above having one or two R groups (e.g., TMS groups) coupled to the N4 amino group.

In one representative embodiment, the N-silylated pyrimidine prodrug has the structure:

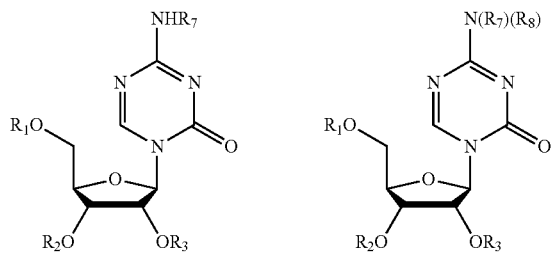

wherein R₁, R₂, R₃, R₇, and R₈ are independently selected from hydrogen or Si(R₄)(R₅)(R₆), wherein R₄, R₅, and R₆ are independently selected from hydrogen or alkyl, provided that at least one of R₁, R₂, R₃, R₇, or R₈ is Si(R₄)(R₅)(R₆). In one embodiment, R₄, R₅, and R₆ are methyl.

In the silylated-pyrimidine compounds of the invention described above, the term "alkyl" refers to the alkyl group of the trialkylsilyl group and is a C1-C10 alkyl group (e.g., methyl, ethyl, n-propyl, i-propyl, n-butyl, s-butyl, i-butyl, t-butyl) that may be a straight chain, branched, or cyclic alkyl group. In certain embodiments, the alkyl group is a C1-C4 alkyl group. In certain specific embodiments, the alkyl group is a methyl group. In certain embodiments, each alkyl group of the trialkylsilyl group is the same (e.g., trimethylsilyl). In other embodiments, the trialklysilyl group includes two or three different alkyl groups (e.g., t-butyldimethylsilyl).

The present disclosure provides representative silylated therapeutic pyrimidine compounds. In view of the teaching of the present invention set forth herein, it will be appreciated that the present invention includes silylated versions of therapeutic pyrimidine compounds (i.e., silylated therapeutic pyrimidine compounds). Many therapeutic pyrimidine compounds are known in the art, as well as their usefulness and limitations. The present invention addresses those limitations by providing a novel class of therapeutic pyrimidine compounds: silylated therapeutic pyrimidine compounds. The silylated therapeutic pyrimidine compounds of the invention provide advantageous and previously unachievable and advantageous properties to therapeutic pyrimidine compounds. The advantages of the representative silylated pyrimidine compounds enumerated and demonstrated herein accrue to silylated therapeutic pyrimidine compounds. The effect of silylation is to render the therapeutic pyrimidine compounds hydrophobic and readily administered using the compositions of the invention. In certain aspects, the silylated pyrimidine compounds of the invention are prodrugs: releasing the de-silylated compound (i.e., therapeutic pyrimidine compound) in vivo (e.g., by hydrolysis of the Si—O bond). As such the silylated therapeutic compounds of the invention are readily administered, have increased bioavailability, and can be advantageously delivered to the site of action for improved effectiveness.

In another aspect of the invention, methods for making the silylated-pyrimidine prodrugs are provided. The silylated-pyrimidine compounds of the invention can be made by treating a pyrimidine compound with a silylating agent, such as those known in the art (e.g., trimethylsilyl chloride). In certain embodiments, for pyrimidine compounds having silyl-reactive amine and hydroxyl groups, the silylated-pyrimidine compounds of the invention have both amine groups and hydroxy groups silylated. In other embodiments, for pyrimidine compounds having silyl-reactive amine and hydroxyl groups, the silylated-pyrimidine compounds of the invention have only hydroxy groups silylated.

The preparation of 2',2'-difluoro-5-azadeoxycytidine is provided in Example 1. The preparation of 2',2'-difluoro-5,6-dihydro-5-azadeoxycytidine is provided in Example 2. The preparation of 2',2'-difluorozebularine is provided in Example 3. The preparation of 2',2'-difluorodeoxyribose-trifluorothymidine is provided in Example 4. Silylated-pyrimidine prodrugs of the invention can be made by treating a pyrimidine analog with an excess of trimethylsilyl chloride and triethylamine in tetrahydrofuran. Alternatively, silylated-pyrimidine prodrugs of the invention can be made by treating a pyrimidine analog with an excess of 1,1,1,3,3,3-hexamethyldisilazane and catalytic amounts of ammonium sulfate at 125° C. The preparation of a representative silylated-pyrimidine prodrug, 2',2'-difluoro-5-azadeoxycytidine-trimethylsilyl, is provided in Example 5.

In other aspects, the present invention provides pharmaceutical compositions comprising at least one silylated-pyrimidine prodrug of the invention together with a pharmaceutically acceptable carrier suitable for administration to a human or animal subject, either alone or together with other therapeutics and/or anticancer agents. The silylated-pyrimidine prodrugs of the invention may be formulated into a composition that additionally comprises suitable pharmaceutically acceptable carriers, including excipients and other compounds that facilitate administration of the silylated-pyrimidine prodrugs to a mammalian subject.

In one embodiment of the invention, the pharmaceutically acceptable carrier is a lipophilic medium. The lipophilic medium can be any one of a variety of lipophilic mediums including, for example, oils. In one embodiment, the lipophilic medium includes a tocopherol (e.g., α-tocopherol). In one embodiment, the lipophilic medium includes corn oil. Representative oils useful as the lipophilic medium include the following:

Fatty acids and esters thereof, including carboxylic acids of various chain lengths, mostly straight chain, but which could be branched, examples of which include capric, caprylic, caproic, lauric, myristic, stearic, oleic, linoleic, behenic, and as well as saturated or unsaturated fatty acids and esters;

Fatty acids esterified with glycerin to form mono-, di-, or triglycerides, which can be synthetic or derived from natural sources, including, but not limited to, for example, glycerides such as soybean oil, cottonseed oil, rapeseed oil, fish oil, castor oil, Capmul MCM, Captex 300, Miglyol 812, glyceryl monooleate, triacetin, acetylated monoglyceride, tristearin, glyceryl behenate, and diacetyl tartaric acid esters of monoglycerides;

Glycerides conjugated to other moieties, such as polyethylene glycol (for example, Labrasol, Labrafac, Cremophor EL);

Phospholipids, either natural or synthetic, such as dimyristyl phosphatidylcholine, egg lecithin, and pegylated phospholipids;

Other fatty esters including fatty alcohols (myristyl myristate, isopropyl palmitate), or sugars (sorbitan monooleate, SPAN 80, Tween 80, sucrose laurate);

Fatty alcohols such as stearyl alcohol, lauryl alcohol, benzyl alcohol, or esters or ethers thereof, such as benzyl benzoate;

Fat-soluble vitamins and derivatives, for example, vitamin E (including all of the tocopherols and tocotrienols, and tocopherol and tocotrienol derivatives, such as vitamin E succinate, vitamin E acetate, and vitamin E succinate polyethylene glycol (TPGS)).

In certain embodiments, the silylated-pyrimidine compounds of the invention can be formulated in an emulsion, such as a nanoemulsion. The concentration of the silylated-pyrimidine compound can vary depending on the compound, the emulsion components, and the desired concentration to be administered (e.g., 0.5 to about 10 mg/mL). Oil droplet size in the emulsion can also be varied as necessary (e.g., 10 to 200 nm or less than 100 nm). A nanoemulsion comprising a representative silylated-pyrimidine compound of the invention (NUC041) is described in Example 5.

In another aspect, the present invention provides methods of treating human or animal subjects suffering from a cellular proliferative disease such as cancer. Representative cell proliferative diseases treatable by the compounds of the invention include hematologic cancers, such as leukemia, lymphoma, and myeloma, and nonhematologic cancers, such as solid tumor carcinomas (e.g., breast, ovarian, pancreatic, colon, colorectal, non-small lung and bladder), sarcomas, and gliomas. The present invention provides methods of treating a human or animal subject in need of such treatment, comprising administering to the subject a therapeutically effective amount of one or more silylated-pyrimidine prodrugs of the invention, either alone or in combination with one or more other therapeutic and/or anticancer agents.

Compositions that include one or more silylated-pyrimidine prodrugs of the invention are administered to deliver therapeutically effective amounts of the silylated-pyrimidine prodrug. Therapeutically effective amounts of the silylated-pyrimidine prodrug(s) will generally range up to the maximally tolerated dosage, but the concentrations are not critical and may vary widely. The precise amounts employed by the attending physician will vary, of course, depending on the compound, route of administration, physical condition of the patient and other factors. The daily dosage may be administered as a single dosage or may be divided into multiple doses for administration. Administration of the silylated-pyrimidine prodrugs of the invention is accomplished by any effective route, for example, parenterally or orally.

The amount of the silylated-pyrimidine prodrugs of the invention actually administered will be a therapeutically effective amount, which term is used herein to denote the amount needed to produce a substantial beneficial effect. Effective doses may be extrapolated from dose-response curves derived from in vitro or animal model test systems. The animal model is also typically used to determine a desirable dosage range and route of administration. Such information can then be used to determine useful doses and routes for administration in humans or other mammals. The determination of an effective dose is well within the capability of those skilled in the art. Thus, the amount actually administered will be dependent upon the individual to which treatment is to be applied, and will preferably be an optimized amount such that the desired effect is achieved without significant side-effects.

The following examples are provided for the purpose of illustrating, not limiting, the invention.

EXAMPLES

Example 1

The Preparation of 2',2'-Difluoro-5-azadeoxycytidine

Two alternative pathways, shown in Scheme I, were used to prepare 2',2'-difluoro-5-azadeoxycytidine (Compound IV).

A. Preparation of 3',5'-dibenzoyl-2',2'-difluoro-5-azadeoxycytidine (Compound III) Via 1-bromo-2-deoxy-2,2-difluoro-D-ribofuranosyl-3,5-dibenzoate (Compound I)

(1). The starting material, 2-deoxy-2,2-difluoro-D-ribofuranosyl-3,5-dibenzoate known in the art (Chou et. al., Synthesis 1992, pp. 565-570) was converted to 1-bromo analog by a method similar to the one described in WO 2006/070985. The starting ribose (3.9 g, 10.3 mmol) was dissolved in 31 ml of toluene and dry triethylamine (1.43 ml, 10.3 mmol) was added. The solution was cooled to 0° C. and diphenyl phosphoryl chloride (2.64 ml, 12.3 mmol) in 8 ml of toluene was added during 15 min. The reaction mixture was warmed up to room temperature and incubated for 3.5 hours. The reaction was quenched by addition of 1 M HCl (10.2 ml), the toluene layer was separated and aqueous layer was extracted back with 10 ml ether. The organic layers were combined, extracted consequently with water, saturated $NaHCO_3$, and saturated NaCl (each 20 ml) and dried over $MgSO_4$. The solvents were removed and the product was isolated by flash chromatography on silica gel in hexane-ethyl acetate gradient. Yield 4.6 g, 73%.

(2). To the intermediate diphenylphosphate analog (4.6 g, 7.5 mmol) prepared as described in Step (1), was added HBr in acetic acid (30%, 16.2 ml, 81.3 mmol) and the reaction mixture was incubated for 6.5 h at room temperature. The reaction mixture was diluted with 80 ml of methylene chloride and extracted twice with ice water, saturated $NaHCO_3$, and saturated NaCl (each 100 ml). The organic layer was dried with $MgSO_4$, filtered and evaporated to yield 1-bromo-2-deoxy-2,2-difluoro-D-ribofuranosyl-3,5-dibenzoate (Compound I, 3.1 g, 93%), which is a 9:1 mixture of α and β isomers.

(3). 5-Azacytosine (98%, Aldrich, 5.0 g, 44.8 mmol) and ammonium sulfate (25 mg) were suspended in hexamethyldisilazane (25 ml) and chlorotrimethylsilane (0.2 ml) was added. The reaction mixture was heated at the reflux for 17 h. The clear solution was cooled, evaporated, co-evaporated twice with dry xylene and vacuum dried to yield whitish solids of the silylated 5-azacytosine (~7 g), which is used in whole for the next glycosylation step.

(4). For glycosylation step 1-bromo-2-deoxy-2,2-difluoro-D-ribofuranosyl-3,5-dibenzoate (Compound I) (0.78 g, 1.77 mmol), prepared as described in Step (2), was dissolved in 4 ml anisole and transferred to the silylated 5-azacytosine solids prepared as in Step (3). The suspension was heated to 150° C. and 2 ml of anisole was added to complete dissolution of all solids. After 4 hours the reaction mixture was cooled and $SnCl_4$ (0.2 ml, 2 mmol) was added. The reaction mixture was reheated to 150° C. for 6 hours, cooled to room temperature, quenched by addition of methylene chloride (30 ml), methanol (10 ml) and silica gel (20 g) and dried to yield 3',5'-dibenzoyl-2',2'-difluoro-5-azadeoxycytidine (Compound III). The resulting powder was applied on the top of the packed silica gel column and products were isolated by flash chromatography in chloroform-methanol gradient. β-Isomer was eluted first followed by α-isomer (only partial separation was achieved, yield for β-isomer 12%, α-isomer 5%). Complete isomer separation was achieved by RP HPLC on Gemini C18 5u (21.2×250 mm column) in 50 mM triethylammonium acetate (pH 7.5)-acetonitrile gradient.

$^1$H NMR in $CDCl_3$ for compound III β-isomer: 8.12 ppm (s, 1H, H6), 7.8-8.1 (m, 4H, benzoyl), 7.4-7.6 (m, 2H, benzoyl), 7.2-7.4 (m, 4H, benzoyl), 6.38 (br. t, J=8.0 Hz, 1H, H1'), 5.65 (m, 1H, H3'), 4.70 (m, 2H, H5'), 4.58 (m, 1H, H4'). ESI MS: 473.3 $[M+H]^+$, 471.1 $[M-H]^-$.

B. Preparation of 2',2'-difluoro-5-azadeoxycytidine (Compound IV)

3',5'-dibenzoyl-2',2'-difluoro-5-azadeoxycytidine (Compound III) (15 mg, 3:1 mixture of α and β isomers), prepared as in Step A, was dissolved in 2 ml of anhydrous MeOH and 1 M NaOMe in MeOH (0.1 ml) was added. After 1 h at room temperature, the reaction mixture was evaporated and the deprotected isomers were isolated by RP HPLC on Gemini C18 5u (21.2×250 mm column) in 50 mM triethylammonium acetate (pH 7.5)-acetonitrile gradient. Immediately after separation fractions corresponding to β isomer were pooled and evaporated at below 10° C. to yield 0.4 mg (19%) of 2',2'-difluoro-5-azadeoxycytidine (Compound IV).

$^1$H NMR in DMSO-$d_6$ for compound IV β-isomer: 8.48 ppm (s, 1H, H6), 7.79 (br, 2H, $NH_2$), 6.35 (br, 1H, 3'OH), 6.07 t, J=8.0 Hz, 1H, H1'), 5.30 (br, 1H, 5'-OH), 4.90 (br, 1H, 5'-OH), 4.23 (br. m, 1H, H3'), 3.85 (m, 1H, H4'), 3.78 (m, 1H, H5'), 3.63 (m, 1H, H5'), UV 240 nm (sh) in 50 mM triethylammonium acetate (pH 7.5)

C. Preparation of 3',5'-dibenzoyl-2',2'-difluoro-5-azadeoxycytidine (Compound III) Via 1-methylsulfonyl-2-deoxy-2,2-difluoro-D-ribofuranosyl-3,5-dibenzoate (Compound II)

Silylated 5-azacytosine (2.3 g, 9 mmol) prepared as described in Step A(3), was dissolved in 2 ml of anisole at 130° C. 1-Methylsulfonyl-2-deoxy-2,2-difluoro-D-ribofuranosyl-3,5-dibenzoate (Compound II) (0.4 g, 0.87 mmol), prepared as described by Chou et. al., Synthesis 1992, pp. 565-570, was dissolved in 1 ml of anisole and was added to the hot solution of the silylated 5-azacytosine. The reaction mixture was incubated at 150° C. for 7 hours, cooled to room temperature, quenched by addition of 15 ml methylene chloride, 15 g silica gel and 5 ml methanol and the suspension was dried on vacuum. The resulting powder was applied on the top of the packed silica gel column and products were isolated by flash chromatography in chloroform-methanol gradient. Appropriate fractions were pooled and evaporated to yield 3',5'-dibenzoyl-2',2'-difluoro-5-azadeoxycytidine (Compound III) as 2:1 mixture of α- and β-isomers (100 mg, 25% yield).

D. Preparation of 2',2'-difluoro-5-azadeoxycytidine (Compound IV)

3',5'-dibenzoyl-2',2'-difluoro-5-azadeoxycytidine (Compound III) (80 mg, 2:1 mixture of α and β isomers), prepared as in Step C, was dissolved in 2 ml of anhydrous MeOH and 1 M NaOMe in MeOH (0.1 ml) was added. After 1 h at room temperature, the reaction mixture was evaporated and the deprotected isomers were isolated by RP HPLC on Gemini C18 5u (21.2×250 mm column) in 50 mM triethylammonium acetate (pH 7.5)-acetonitrile gradient. Immediately after separation fractions corresponding to β isomer were pooled, evaporated at below 10° C. to yield 2.1 mg (13%) of 2',2'-difluoro-5-azadeoxycytidine (Compound IV).

RP HPLC retention time and spectral characteristics (i.e., $^1$H NMR and UV) for Compound IV were the same as in Step B. ESI MS: 265.2 [M+H]$^+$.

A. Preparation of 3',5'-dibenzoyl-2',2'-difluoro-5-azadeoxycytidine (Compound V)

Pure β-Isomer of 3',5'-dibenzoyl-2',2'-difluoro-5-azadeoxycytidine (Compound III) (144 mg, 0.30 mmol), prepared as in Example 1, was dissolved in 3 ml of methylene chloride and triethylamine (0.12 ml) and chlorotrimethysilane (0.1 ml) were added. After 0.5 hour the reaction mixture was diluted with 5 ml acetic acid and sodium borohydride

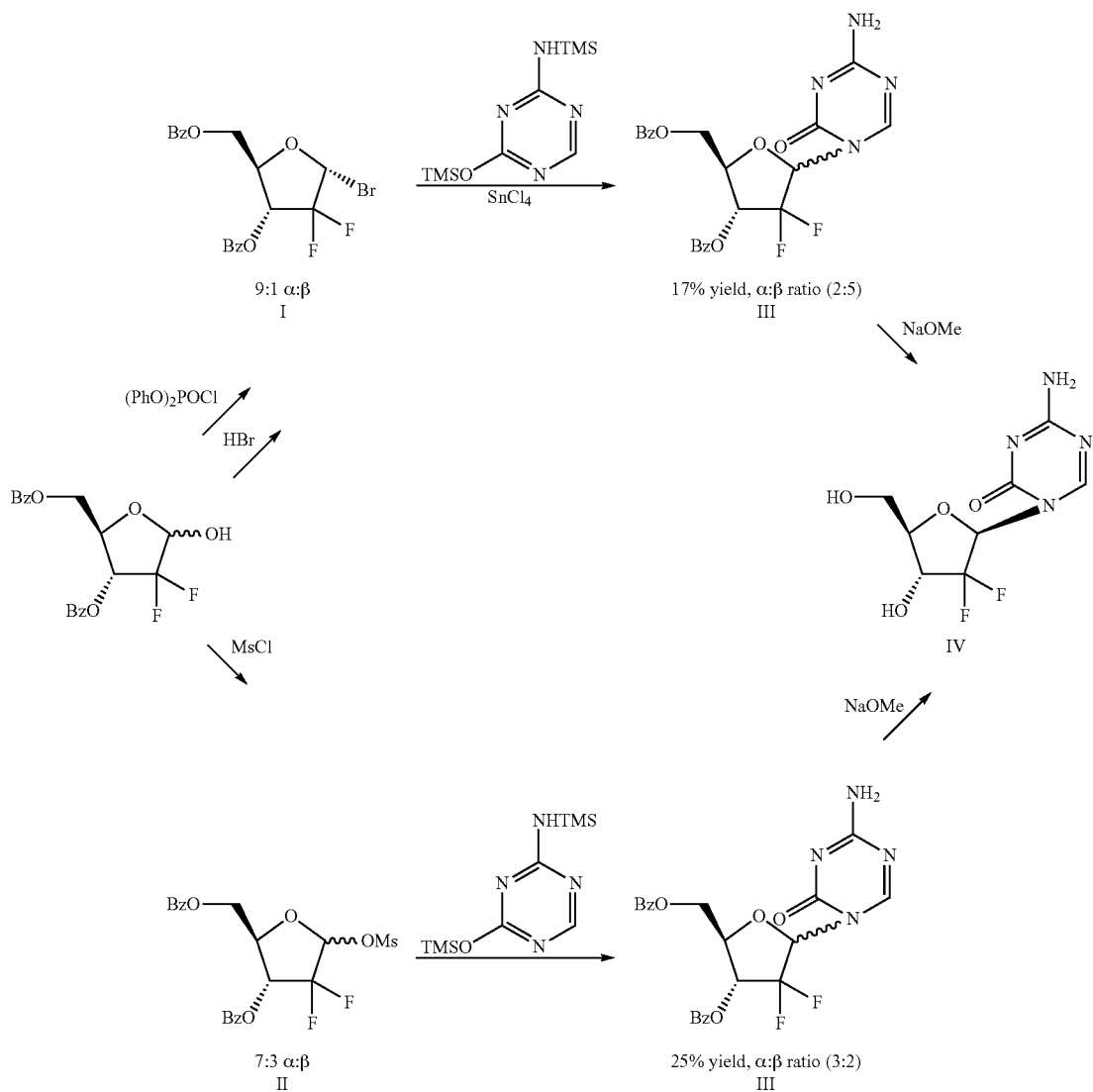

Scheme 1. Synthesis of 3',5'-dibenzoyl-2',2'-difluoro-5-azadeoxycytidine (Compound III) and 2',2'-difluoro-5-azadeoxycytidine (Compound IV).

Ms = methylsulfonyl; TMS = trimethylsilyl; Bz = benzoyl; Ph = phenyl; Me = methyl Example 2

The Preparation of 2',2'-Difluoro-5,6-dihydro-5-azadeoxycytidine

The preparation of 2',2'-difluoro-5,6-dihydro-5-azadeoxycytidine (Compound VI) is shown in Scheme 2.

(100 mg, 2.6 mmol) was added as powder. After 1 h at room temperature the reaction mixture was evaporated and separated by RP HPLC on Gemini C18 5u (21.2×250 mm column) in 50 mM triethylammonium acetate (pH 7.5)-acetonitrile gradient. Fractions corresponding to the product were pooled and evaporated to yield 83 mg (57%) of 3',5'-dibenzoyl-2',2'-difluoro-5-azadeoxycytidine (Compound V).

$^1$H NMR in DMSO-$d_6$ for compound V β-isomer: 7.93-8.07 (m, 4H, benzoyl), 7.64-7.77 (m, 2H, benzoyl), 7.47-7.62 (m, 4H, benzoyl), 6.08 (t, J=7.2 Hz, 1H, H1'), 5.63 (m, 1H, H3'), 4.55-4.70 (m, 3H, H4' and H5'), 4.48 (s, 2H, CH$_2$). ESI MS: 475.4 [M+H]$^+$.

B. Preparation of 2',2'-difluoro-5,6-dihydro-5-azadeoxycytidine (Compound VI)

3',5'-dibenzoyl-2',2'-difluoro-5-azadeoxycytidine (Compound V) (80 mg, 0.168 mmol), prepared as in Step A, was dissolved in 6 ml of anhydrous MeOH and 1 M NaOMe in MeOH (0.3 ml) was added. After 1 h at room temperature, the reaction mixture was quenched by addition of acetic acid (0.02 ml), evaporated and the deprotected product was isolated by RP HPLC on Gemini C18 5u (21.2×250 mm column) in 50 mM triethylammonium acetate (pH 7.5)-acetonitrile gradient. Appropriate fractions were pooled and evaporated to yield 49 mg (95% yield) of 2',2'-difluoro-5,6-dihydro-5-azadeoxycytidine (Compound VI).

$^1$H NMR in DMSO-$d_6$ for compound VI: 5.87 (dd, J$_1$=9.6 Hz, J$_2$=10.8 Hz, 1H, H1'), 4.51 and 4.29 (AB, 2H, CH$_2$), 3.98 (ddd, J$_1$=8.4 Hz, J$_2$=12.8 Hz, J$_3$=12.8 Hz, 1H, H3'), 3.67 (m, 1H, H5'), 3.58 (m, 1H, H4'), 3.52 (m, 1H, H5'). ESI MS: 267.0 [M+H]$^+$.

Scheme 2. Synthesis of 2',2'-difluoro-5,6-dihydro-5-azadeoxycytidine (Compound VI).

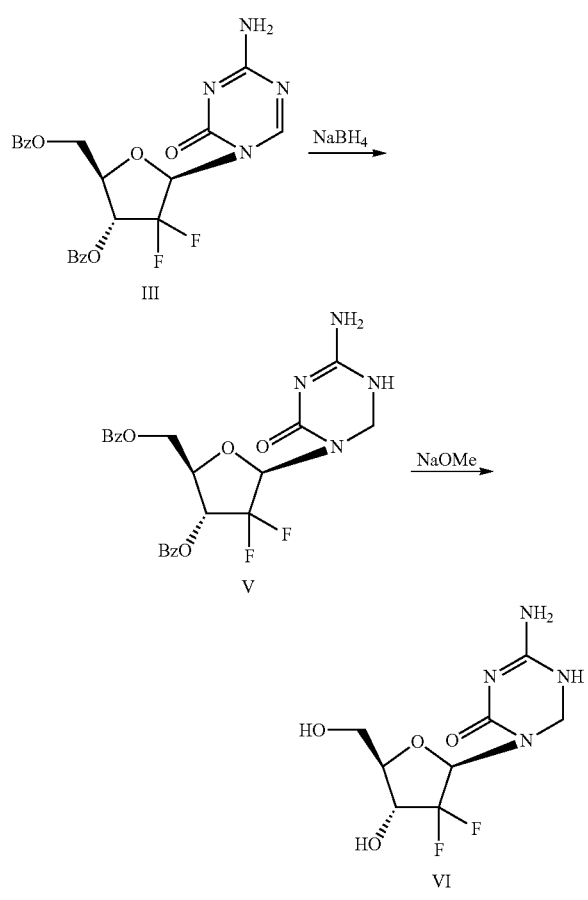

Example 3

The Preparation of 2',2'-Difluorozebularine

The preparation of 2',2'-difluorozebularine (Compound VIII) is shown in Scheme 3.

(1). The starting material 1-bromo-2-deoxy-2,2-difluoro-D-ribofuranosyl-3,5-dibenzoate (Compound I) was prepared as described in the Example 1.

(2). 2-Hydroxypyrimidine hydrochloride (0.57 g, 4.3 mmol) was suspended in hexamethyldisilazane (10 ml). The reaction mixture was heated at reflux for 1.5 h. The clear solution was decanted under argon, evaporated, co-evaporated twice with dry xylene and vacuum dried.

(3). For glycosylation step, 1-bromo-2-deoxy-2,2-difluoro-D-ribofuranosyl-3,5-dibenzoate (Compound I) (1.20 g, 2.7 mmol), prepared as in Step (1), was dissolved in 20 ml of dichloroethane and transferred to the flask containing the silylated 2-hydroxypyrimidine. The reaction mixture was refluxed under argon for 16 hr, then dichloroethane was replaced with 10 mL of anisole, and the temperature was raised to 150° C. The reaction mixture was stirred at 150° C. for 18 hr, cooled to room temperature, and the product, 1-β-(2'-deoxy-2',2'-difluoro-D-ribofuranosyl)-pyrimidine-2-one (Compound VII), was isolated as a mixture of β- and α-isomers (1:6) by flash chromatography on silica gel in methanol/chloroform (3:97). Yield: 0.09 g or 7%.

(4). 1-β-(2'-deoxy-2',2'-difluoro-D-ribofuranosyl)pyrimidine-2-one (Compound VII), prepared as in Steps (1) to (3), (85 mg, 6:1 mixture of α and β isomers) was dissolved in 2 ml of anhydrous MeOH and 1 M NaOMe in MeOH (0.1 ml) was added. After 1 h at 4° C., the reaction mixture was evaporated and the deprotected isomers were isolated by RP HPLC on Gemini C18 5u (21.2×250 mm column) in 50 mM triethylammonium acetate (pH 7.5)-acetonitrile gradient. Immediately after separation fractions corresponding to β isomer were pooled and evaporated to yield 3.4 mg (7.4%) of 2',2'-difluorozebularine (Compound VIII).

$^1$H NMR in DMSO-$d_6$ for compound VIII β-isomer: 8.66 ppm (dd, J$_1$=4 Hz, J$_2$=2.4 Hz, 1H), 8.57 (dd, J$_1$=6.8 Hz, J$_2$=2.4 Hz, 1H), 6.62 (dd, J$_1$=6.8 Hz, J$_2$=4 Hz, 1H), 6.07 (t, J=7.2 Hz, 1H), 4.42-4.29 (m, 1H), 4.05-3.97 (m, 2H), 3.88-3.82 (m, 1H). ESI MS: 249 [M+H]$^+$.

Scheme 3. Synthesis of 2',2'-difluorozebularine (Compound VIII).

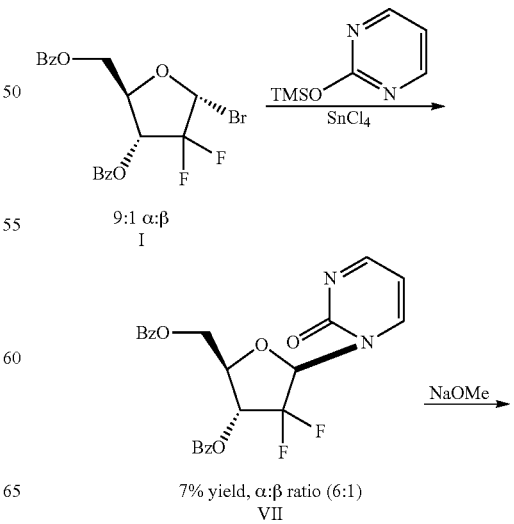

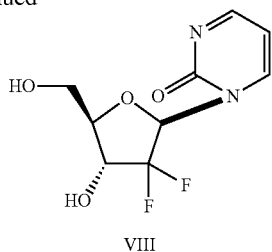

VIII

Example 4

Preparation of 2',2'-Difluorodeoxyribose-trifluorothymidine

The preparation of 2',2'-difluorodeoxyribose-trifluorothymidine (Compound X) is shown in Scheme 4. 2',2'-Difluorodeoxyribose-trifluorothymidine (Compound X) is prepared by glycosylation of silylated 5-(trifluoromethyl)uracil with 1-bromo-2-deoxy-2,2-difluoro-D-ribofuranosyl-3,5-dibenzoate (Compound I), prepared as in Example 1, in anisole using $SnCl_4$ as catalyst followed by deprotection with catalytic amounts of sodium methoxide in methanol.

Scheme 4. Synthesis of 2',2'-difluorodeoxyribose-trifluorothymidine (Compound X).

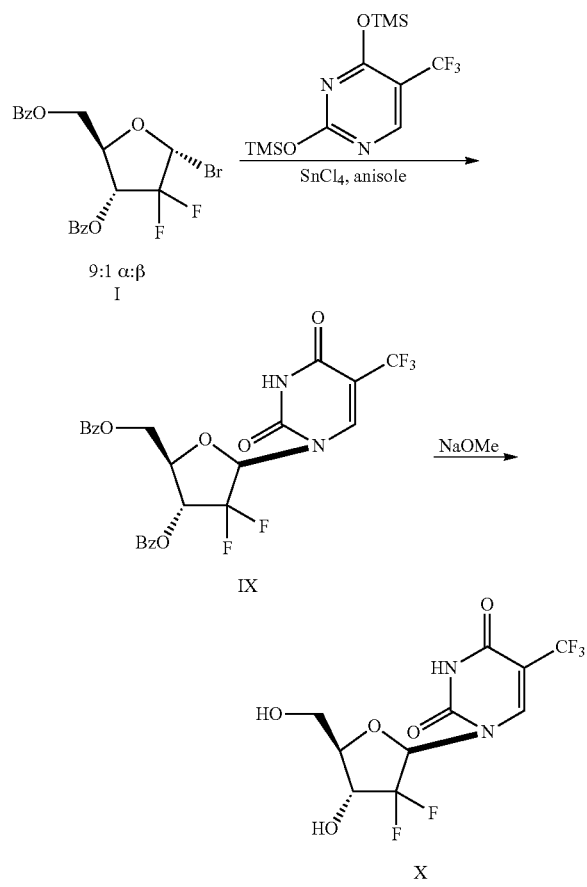

Example 5

The Preparation of a Representative Silylated-Pyrimidine Prodrug: 2',2'-Difluoro-5-azadeoxycytidine-trimethylsilyl (NUC041)

Method I. The preparation of 2',2'-difluoro-5-azadeoxycytidine-trimethylsilyl (Compound XI) is shown in Scheme 5. 2',2'-Difluoro-5-azadeoxycytidine-trimethylsilyl (Compound XI) is prepared by treating 2',2'-difluoro-5-azadeoxycytidine (Compound IV), prepared as in Example 1, with excess of trimethylsilyl chloride and triethylamine in tetrahydrofuran.

Scheme 5. Synthesis of 2',2'-difluoro-5-azadeoxycytidine-trimethylsilyl (Compound XI)

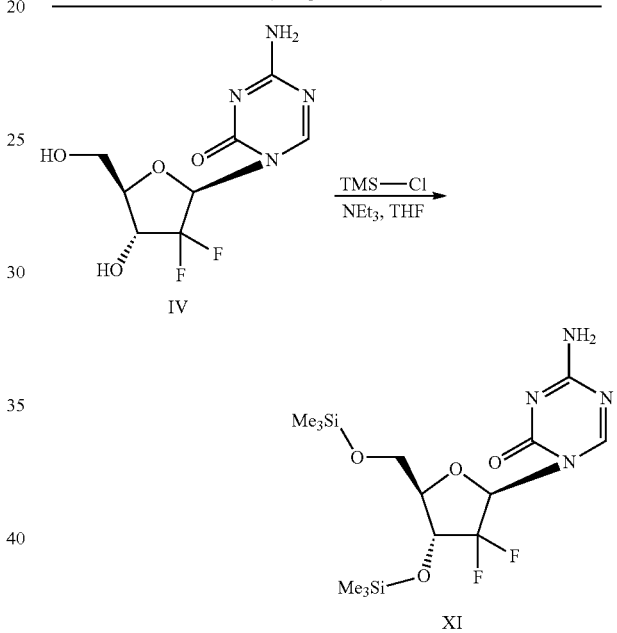

Method II. An alternative method to prepare 2',2'-difluoro-5-azadeoxycytidine-trimethylsilyl (Compound XI) is as follows. 2',2'-difluoro-5-azadeoxycytidine-trimethylsilyl (Compound XI) is prepared by treating 2',2'-difluoro-5-azadeoxycytidine (Compound IV), prepared as in Example 1, with excess of 1,1,1,3,3,3-hexamethyldisilazane and catalytic amounts of ammonium sulfate at 125° C. The product is isolated by flash chromatography.

Compound XI was successfully formulated in a nanoemulsion at a concentration of 3 mg/ml. The nanoemulsion has an oil phase consisting of an injectable oil and lecithin and an aqueous phase comprising a tonicity adjuster, a stabilizer and water. The emulsions are of oil-in-water type with the mean oil droplets less than 100 nm. Each vehicle is at neutral pH (5-7) and about isotonic. The toxicity of formulated Compound XI was tested in mice. Mice were injected intravenously on three consecutive days with Compound XI at doses of up to 60 mg/kg and observed at the end of one week. No evidence of toxicity was noted as measured by weight loss.

Example 6

Representative Silylated-Pyrimidine Prodrug: 2',3',5'-Tri(trimethylsilyl)-5-azacytidine (NUC025)

In this example the characteristics of a representative silylated-pyrimidine prodrug of the invention, 2',3',5'-tri(trimethylsilyl)-5-azacytidine (NUC025), is described. The structure of NUC025 is shown below.

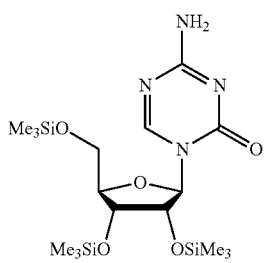

2',3',5'-Tri(trimethylsilyl)-5-azacytidine (NUC025) is prepared by a method analogous to the preparation of 2',2'-difluoro-5-azadeoxycytidine-trimethylsilyl described above in Example 5.

The in vitro cytotoxicity of NUC025 is compared to 5-azacytidine for breast, colon, and leukemia in Table 1.

Table 1. In vitro cytotoxicity of NUC025 and 5-azacytidine ($IC_{50}$ in μM).

TABLE 1

In vitro cytotoxicity of NUC025 and 5-azacytidine ($IC_{50}$ in μM).

| Compound | Breast MDA-MB-231 | Colon HCT-116 | Leukemia L1210 |
|---|---|---|---|
| NUC025 | 3.28 | 1.08 | 1.18 |
| 5-azacyctidine | 1.64 | 0.62 | 1.7-2.4 |

The data in Table 1 show that NUC025 preserves the activity of 5-azacytidine in vitro. Such prodrugs of 5-aza nucleosides may demonstrate superiority in vivo, where a longer circulating half-life in important.

FIG. 1 illustrates the release of 5-azacytidine from the 5-azacytidine-TMS prodrug (NUC025) by hydrolysis, suggesting that, at least in PBS at room temperature, approximately 80% of the active drug can be recovered.

While illustrative embodiments have been illustrated and described, it will be appreciated that various changes can be made therein without departing from the spirit and scope of the invention.

The embodiments of the invention in which an exclusive property or privilege is claimed are defined as follows:

1. A compound having the formula:

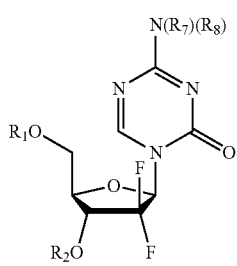

wherein $R_1$, $R_2$, $R_7$, and $R_8$ are independently selected from hydrogen or $Si(R_4)(R_5)(R_6)$, wherein $R_4$, $R_5$, and $R_6$ are independently selected from hydrogen or alkyl, provided that at least one of $R_1$, $R_2$, $R_7$, or $R_8$ is $Si(R_4)(R_5)(R_6)$.

2. The compound of claim 1 having the formula:

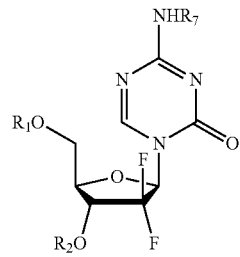

wherein $R_1$, $R_2$, and $R_7$ are independently selected from hydrogen or $Si(R_4)(R_5)(R_6)$, wherein $R_4$, $R_5$, and $R_6$ are independently selected from hydrogen or alkyl, provided that at least one of $R_1$, $R_2$, or $R_7$ is $Si(R_4)(R_5)(R_6)$.

3. The compound of claim 1 having the formula:

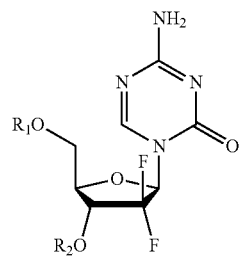

wherein $R_1$ and $R_2$ are independently selected from hydrogen or $Si(R_4)(R_5)(R_6)$, wherein $R_4$, $R_5$, and $R_6$ are independently selected from hydrogen or alkyl, provided that at least one of $R_1$ or $R_2$ is $Si(R_4)(R_5)(R_6)$.

4. The compound of claim 1, wherein $R_1$ and $R_2$ are $Si(R_4)(R_5)(R_6)$ and $R_4$, $R_5$, and $R_6$ are methyl.

5. A pharmaceutical composition, comprising a compound of claim 1 and a pharmaceutically acceptable carrier.

6. A method for delivery of a compound to a tumor site by enhanced permeability and retention, comprising administering an effective amount of a compound having the formula:

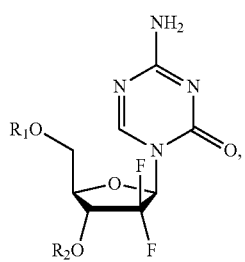

wherein $R_1$ and $R_2$ are $Si(CH_3)_3$, to a tumor site in the subject in need thereof.

7. A method for treating a solid tumor carcinoma, comprising administering an effective amount of a compound having the formula:

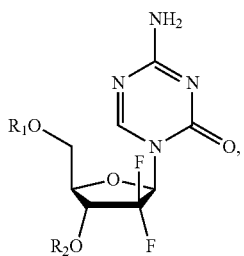

wherein $R_1$ and $R_2$ are $Si(CH_3)_3$, to a subject in need thereof.

8. The method of claim 7, wherein the solid tumor carcinoma is selected from the group consisting of breast, non-small cell lung, and colon carcinomas.

9. The method of claim 6, wherein the subject is a human.

10. The method of claim 7, wherein the subject is human.

11. The compound of claim 4, having the formula:

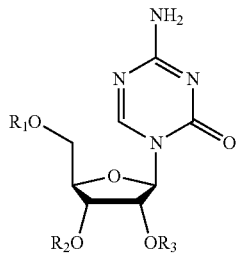

wherein $R_1$ and $R_2$ are $Si(CH_3)_3$.

* * * * *

UNITED STATES PATENT AND TRADEMARK OFFICE
CERTIFICATE OF CORRECTION

PATENT NO. : 10,479,807 B2  
APPLICATION NO. : 15/516653  
DATED : November 19, 2019  
INVENTOR(S) : Richard Daifuku and Dmitri S. Sergueev Page 1 of 1

It is certified that error appears in the above-identified patent and that said Letters Patent is hereby corrected as shown below:

In the Claims

In Claim 11, Column 24, Line 5, delete:

" 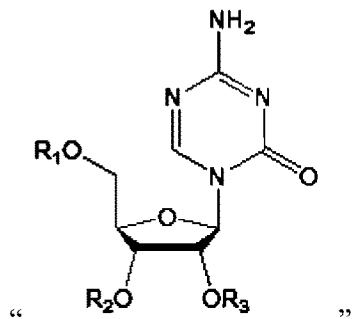 "

And insert:

-- 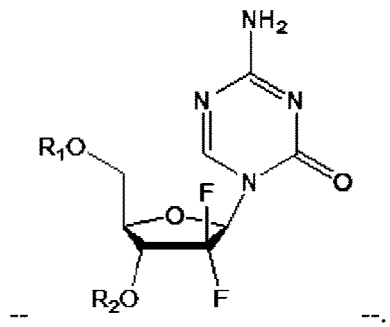 --.

Signed and Sealed this  
Thirty-first Day of December, 2019

Andrei Iancu  
*Director of the United States Patent and Trademark Office*

UNITED STATES PATENT AND TRADEMARK OFFICE
CERTIFICATE OF CORRECTION

PATENT NO. : 10,479,807 B2
APPLICATION NO. : 15/516653
DATED : November 19, 2019
INVENTOR(S) : Richard Daifuku and Dmitri S. Sergueev It is certified that error appears in the above-identified patent and that said Letters Patent is hereby corrected as shown below:

On the Title Page

In Item (73), delete:
"Epigenetics Phrama LLC"

And insert:
-- Epigenetics Pharma LLC --

Signed and Sealed this
Second Day of June, 2020

Andrei Iancu
*Director of the United States Patent and Trademark Office*